(12) United States Patent
Justus et al.

(10) Patent No.: US 8,858,505 B1
(45) Date of Patent: Oct. 14, 2014

(54) CATHETER INJECTION PORT LOCK

(71) Applicants: Jesse Michael Justus, Royal Oak, MI (US); Michael K. Justus, Beloit, WI (US)

(72) Inventors: Jesse Michael Justus, Royal Oak, MI (US); Michael K. Justus, Beloit, WI (US)

( * ) Notice: Subject to any disclaimer, the term of this patent is extended or adjusted under 35 U.S.C. 154(b) by 0 days.

(21) Appl. No.: 14/031,621

(22) Filed: Sep. 19, 2013

Related U.S. Application Data

(60) Provisional application No. 61/809,440, filed on Apr. 8, 2013.

(51) Int. Cl.
*A61M 5/32* (2006.01)
*A61M 5/50* (2006.01)

(52) U.S. Cl.
CPC .................................... *A61M 5/5086* (2013.01)
USPC .......................................................... 604/174

(58) Field of Classification Search
USPC .......................................... 604/174, 179, 180
See application file for complete search history.

(56) References Cited

U.S. PATENT DOCUMENTS

| | | | |
|---|---|---|---|
| 4,517,971 A * | 5/1985 | Sorbonne ....................... | 128/879 |
| 5,116,324 A * | 5/1992 | Brierley et al. ............... | 604/180 |
| 5,730,418 A * | 3/1998 | Feith et al. .................. | 251/149.6 |
| 6,283,945 B1 * | 9/2001 | Bierman ........................ | 604/174 |
| D609,338 S | 2/2010 | Dozier, Jr. | |
| 7,967,792 B2 * | 6/2011 | Bierman ........................ | 604/174 |
| 8,556,859 B2 * | 10/2013 | Nilson et al. .................. | 604/174 |
| 2006/0247577 A1 * | 11/2006 | Wright ........................... | 604/174 |
| 2007/0219500 A1 * | 9/2007 | Wright et al. .................. | 604/174 |
| 2009/0024090 A2 * | 1/2009 | Wright et al. .................. | 604/174 |
| 2009/0093769 A1 * | 4/2009 | Wright et al. .................. | 604/178 |
| 2011/0067623 A1 * | 3/2011 | Fagan ............................ | 116/201 |
| 2011/0118670 A1 * | 5/2011 | Kay et al. ....................... | 604/177 |
| 2012/0197202 A1 | 8/2012 | Wright et al. | |

OTHER PUBLICATIONS

"The PICC Saddle Device(picclinehousing)" http://www.youtube.com/watch?v=_qwLoD4TOB0, uploaded Feb. 4, 2011. Screen shot and partial transcript.

* cited by examiner

*Primary Examiner* — Aarti B Berdichevsky
(74) *Attorney, Agent, or Firm* — Stiennon & Stiennon

(57) ABSTRACT

A lock for an outpatient's peripherally inserted central catheter (PICC) line limits access to the catheter by patients seeking to abuse injectable narcotics. The lock has two plastic housing halves which slide together, and which define an interior enclosure which receives the catheter line injection port. The housing halves have overlying flanges, through which a fastener extends to secure the device in a closed configuration. The fastener interacts with the flanges in such a way that it cannot be removed without distorting the device and giving evidence of tampering. A zippered sleeve may be provided which surrounds the line leading to the injection port and which has a pull tab which may be engaged within the housing to further prevent access to the line directly.

15 Claims, 3 Drawing Sheets

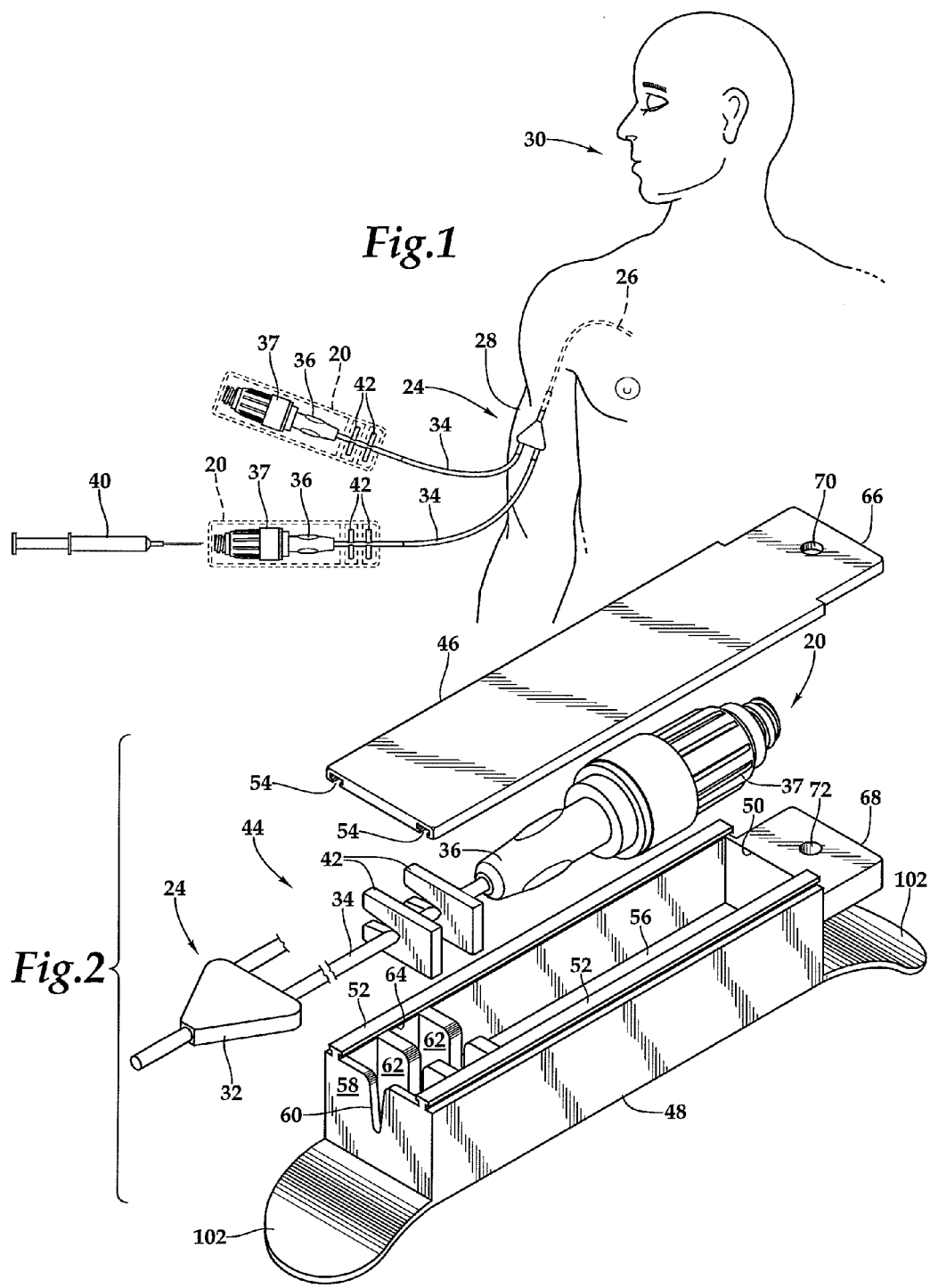

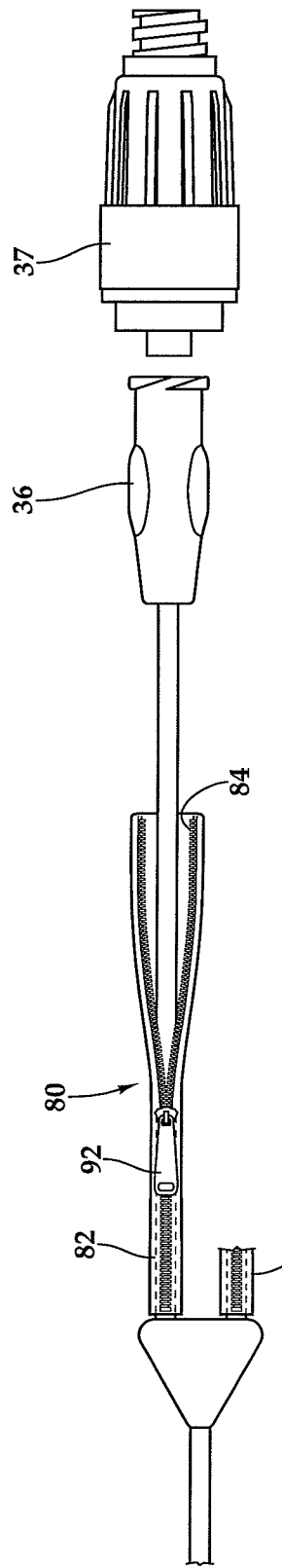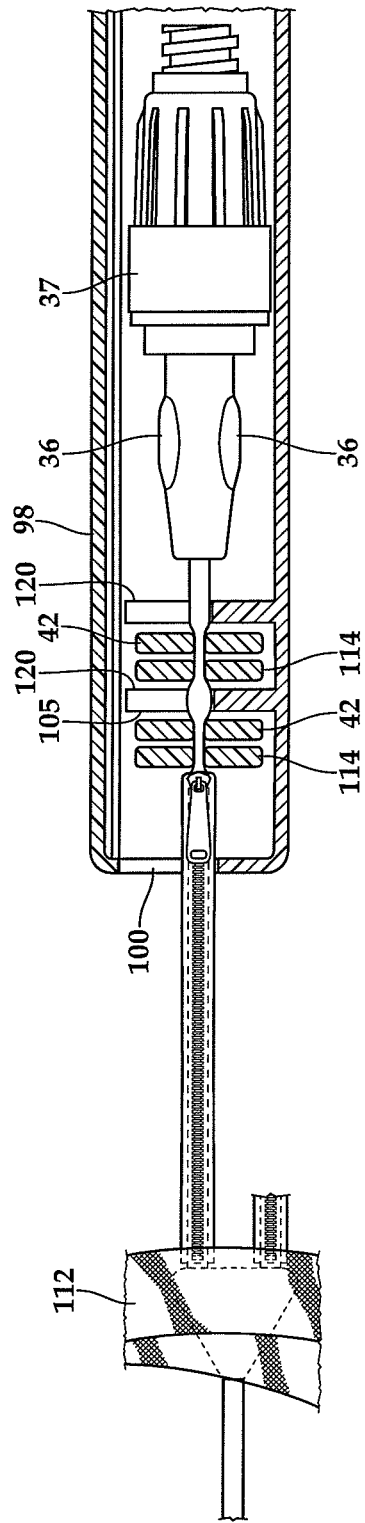

CATHETER INJECTION PORT LOCK

CROSS REFERENCES TO RELATED APPLICATIONS

This application claims the benefit of priority of U.S. provisional patent app. No. 61/809,440, filed Apr. 8, 2013, the disclosure of which is incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

This invention relates generally to catheters with injection ports, such as peripherally inserted central catheters, and more particularly to devices for securing access to them for outpatient safety.

Abusers of intravenous drugs such as heroin are susceptible to severe infections which must be treated by intravenous injection of antibiotics over a course of many weeks. To facilitate this treatment, the drug abuser may be provided with an intravenous peripherally inserted central catheter or PICC line. This catheter, while usually inserted in the hospital, can remain in place for weeks or months, and makes it a simple matter to rapidly inject the necessary antibiotics without difficulty in finding a vein. This ease of intravenous access, however, can be a serious hazard for outpatients who are habitual drug abusers, who can take advantage of this catheter to self-administer unprescribed quantities of narcotics or other controlled substances. Providing a drug abuser with an unsupervised PICC line for outpatient care can lead to illegal drug overdose and death. To protect these high risk patients, who might otherwise not need full-time nursing care, they must be hospitalized and retained under supervision for the multiple weeks that the antibiotics are needed. Hospitalization is vastly more costly than outpatient care, and represents a less than optimal utilization of health care resources.

What is needed is an arrangement which allows drug abusing patients to be safely outfitted with PICC lines for outpatient care.

SUMMARY OF THE INVENTION

The device of the present invention serves as a lock for an outpatient's peripherally inserted central catheter (PICC) line which limits access to the catheter by patients seeking to abuse injectable narcotics. The lock has two plastic housing halves which slide together and which define an interior enclosure which receives a catheter line injection port. The housing halves have overlying flanges, through which a fastener extends to secure the device in a closed configuration. The fastener interacts with the flanges in such a way that it cannot be removed without distorting the device and giving evidence of tampering. The locking mechanism may be a dumbbell shaped metal pin, which is inserted through aligned openings in the aligned flanges by a small handheld press. Each time an intravenous treatment is administered, the pin is extracted by the press and the locking device is destroyed and replaced with a new one. Should the patient remove the box to defeat its restrictions, the damage to the box provides ready evidence to the nurse that the patient has tampered with the device, providing grounds for returning the patient to the hospital.

It is an object of the present invention to provide a device which limits undetected access to the inlet ports of a PICC line.

It is another object of the present invention to provide a tamper-evident lock for a PICC line.

Further objects, features and advantages of the invention will be apparent from the following detailed description when taken in conjunction with the accompanying drawings.

BRIEF DESCRIPTION OF THE DRAWINGS

FIG. 1 is a schematic view of a PICC line in connection with a patient and the function of the PICC line lock of this invention.

FIG. 2 is an exploded isometric view of the PICC line lock of this invention.

FIG. 6 is a perspective view of a sleeve assembly for protecting the PICC line between the inlet port and the base.

FIG. 7 is a fragmentary cross-sectional view of the device of FIG. 6 received within a locked housing.

DESCRIPTION OF THE PREFERRED EMBODIMENTS

Figure 3:
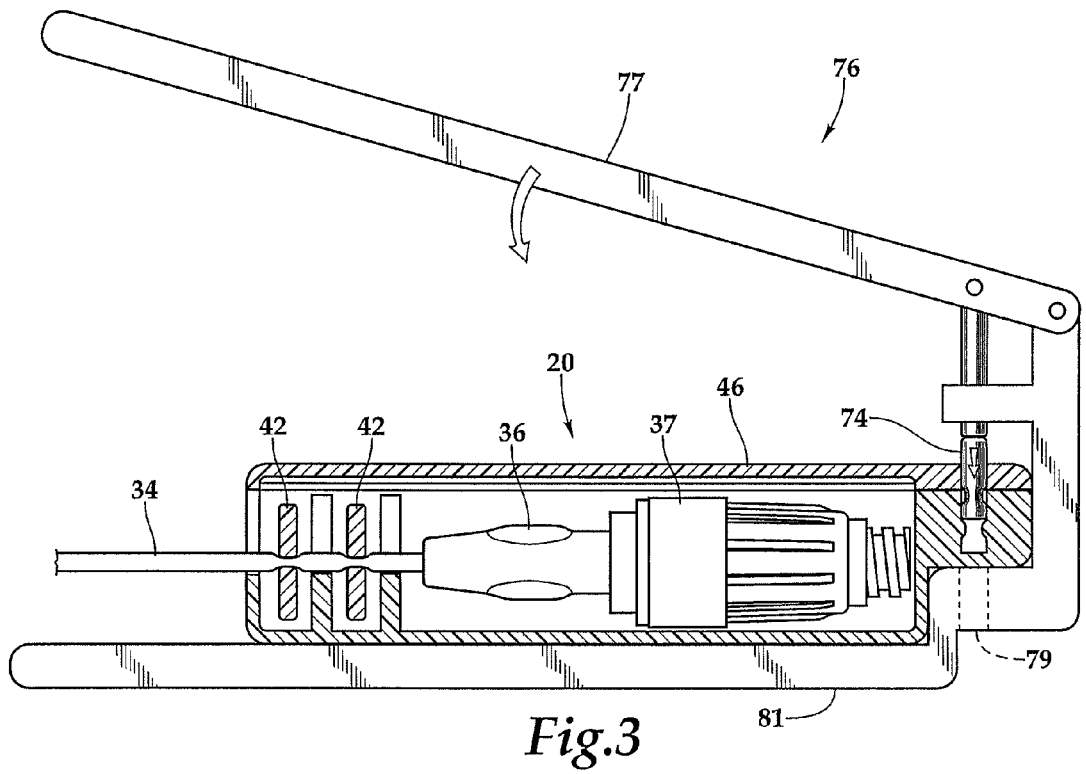
FIG. 3 is an enlarged fragmentary cross-sectional view of the PICC line lock of FIG. 2 as a locking member is being inserted within a hand press.
Figure 4:
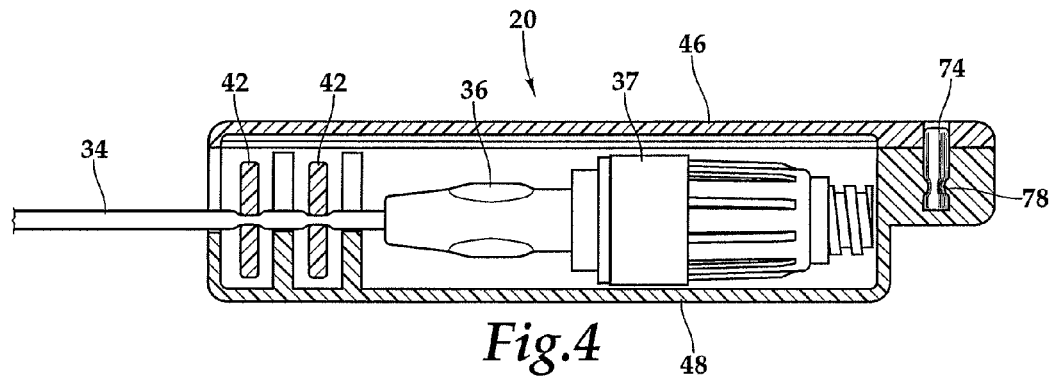
FIG. 4 is a side elevational view of a the device of FIG. 3 in a locked configuration.

Referring more particularly to FIGS. 1-7, where like numbers refer to similar parts, a PICC line lock 20 for use with conventional PICC line assemblies 24 is shown in FIG. 2. A PICC line assembly 24, as shown in FIG. 1, has a catheter 26 which is inserted into an upper extremity 28 of the patient 30, for example an arm. The assembly 24 will typically have a base 32 which is taped to the patient. One or more injection lines 34 extends from the base, each of which is terminated by an inlet port 36. The inlet ports 36 provide an entryway to the injection lines 34 for delivery of fluids from an injection source such as a syringe 40 or a total parenteral nutrition bag or whatever injectable the patient requires. The inlet ports may be provided with a positive displacement connector 37, such as the MaxPlus® clear needleless connector made by Carefusion Corporation of San Diego, Calif., and such as disclosed in U.S. Pat. No. 5,730,418, the disclosure of which is incorporated by reference herein. The lock 20 provides a mechanism for blocking access to the inlet ports 36 by the patient. The injection lines 34 may be provided with one or more mechanical clamps 42 which serve to prevent the escape or entry of liquids into the lines unless the clamps 42 are removed.

As shown in FIG. 2, the lock 20 comprises a box or housing 44 formed by the assembly of a first housing half 46 and a second housing half 48. The housing halves 46, 48 may be injection molded plastic parts formed, for example, of high density polyethylene. The housing halves have cooperating structures which allow the halves to be slid together to define a housing compartment 50 of adequate dimensions to receive an inlet port 36 and any associated connector 37 and to protect the port from access by the patient. The housing 44 may thus be long enough to include a 2-inch long combined inlet port and connector. The second housing half 48 may have two parallel projecting T-rails 52, which are received in two parallel T-slots 54 allowing the two halves to slide together. The second housing half 48 has a bottom wall 56 with a projecting side wall 58 in which is formed a tapered V-shaped slot 60 which serves as a clamp for the injection line leading out of the inlet port which is received within the housing compartment 50. This slot acting as a clamp provides another opportunity to stop the flow of liquids through the line, even if an intermediate clamp should fail.

The second housing half 48 may be provided with an intermediate wall 62 located within the housing compartment 50 which defines a channel 64 between the end wall and the intermediate wall which will receive the conventional clamp 42 that locks the PICC line and which is typically a part of the PICC line assembly. The housing 44 is dimensioned to create a snug fit for the PICC line assembly comprised of the inlet port 36, the positive displacement connector 37, if any, and the attached inlet line 34, so that these components do not have the space to rotate and become dislodged. Even if rotational forces act on the end assembly, the lack of space to expand will not allow the clamps to become dislodged.

The second housing half 48 may have two thin molded lower tabs 102, shown in FIG. 2. The tabs extend from opposite sides of the second housing half and are flexible to conform to a patient's limb to allow adhesive tape to extend over the tabs to permit the housing 44 to be taped to a patient's body.

The first housing half 46 has a first flange 66 which protrudes away from the housing, and the second housing half 48 has a second flange 68 which protrudes beneath the first flange 66. As shown in FIG. 3, the first flange has a cylindrical opening 70 which aligns with a blind cylindrical opening 72 in the second flange 68 when the two housing halves are slid together into a locked configuration. A metal locking fastener 74 is inserted into the aligned openings 70, 72, with a hand press 76, shown in FIG. 3. The hand press 76 has a mechanism similar to a conventional two-hole press, with a lever 77 which may be depressed to drive the locking fastener 74 into place. The fastener 74 may have a narrower-diameter segment 78 which gives it a dumbbell-like shape which allows the plastic of the flanges 66, 68 to deform into the narrower-diameter segment and thus lock the fastener 74 in place and connect the first housing half 46 to the second housing half 48 in such a fashion that the fastener cannot be removed without distorting the device 20 and giving evidence of tampering with the device. To open the housing 44 and remove the fastener 74, the housing is returned to the hand press 76, and the lever 77 is fully depressed to engage the fastener 74 and to drive it out through the lower flange 68 of the housing. A through hole 79 in the lower member 81 of the press 76 allows passage for the fastener therethrough.

Figure 5:
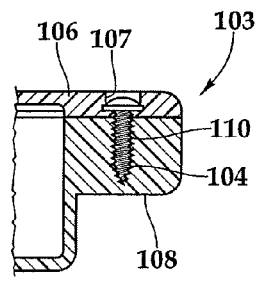
FIG. 5 is a fragmentary cross-sectional view of an alternative embodiment locking mechanism for the PICC line lock of this invention, using a one-way screw.

A housing with an alternate locking mechanism 103 is shown in FIG. 5, which uses a fastener 104 similar to a conventional one-way screw, such as is used in bathroom stalls. The housing has a first flange 106 with a through hole 107 which overlies a second flange 108 with a blind hole 110. The one-way screw fastener can be turned in one direction to be tightened, but cannot be removed without a special tool. When the fastener 104 is fully inserted, portions of the plastic of the upper first flange 106 expand over the outside diameter of the screw head. The base of the screw head's outside diameter acts like a small washer that is integral to the screw head. The lip will expand over the integral washer and lock the screw in place. An authorized person can use a specialized screwdriver to remove the screw. Even if the patient were to gain access to the specialized screwdriver, the deformation of the plastic around the screw head would provide evidence that the housing had been tampered with.

Figure 8:
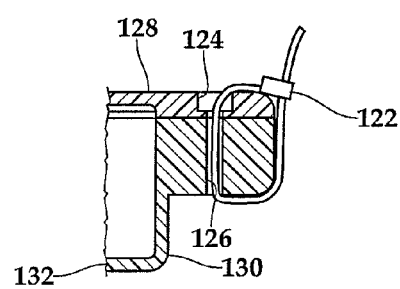
FIG. 8 is a fragmentary cross-sectional view of an alternative embodiment locking mechanism for the PICC line lock of this invention, using a zip tie.

It should be noted that other fasteners may be used the removal of which gives evidence of tampering, for example, as shown in FIG. 8, a zip tie 122 or tie-wrap extending through openings 124, 126 in the halves 128, 130 of the housing 132. A zip tie is a nylon cable tie comprised of a tape section with triangular teeth that slope in one direction. The head of the cable tie has a slot with a flexible pawl that irreversibly rides up the slope of these teeth when the tape is inserted. The pawl engages the backside of these teeth to stop removal of the tape. Typically these ties must be cut to be removed.

Once an injection has been made through the PICC line by an authorized person, the two housing halves are slid together about the inlet port, and then connected with the fastener to lock out access to the inlet port. The lock 20 will stay in place until the authorized person returns on the next visit to administer another injection. To remove the lock 20, the hand press 76 is used to punch out the fastener 74 and thereby allow the housing halves to be slid apart and the inlet ports to be accessed. When the lock 20 is opened, it is destroyed, and cannot be reused. Should a patient attempt to pry apart the housing or otherwise tamper with the lock to separate the housing halves, it would be apparent to the authorized person on the next visit, indicating that the patient was not a suitable candidate for in-home care, and should be returned to hospital care.

To prevent access to the lines 34 between the inlet ports and the base 32 a sleeve assembly 80, shown in FIGS. 6-7, may be provided. The sleeve assembly 80 has a wrap-around sleeve 82 made out of a puncture resistant material, such as plastic or fabric formed of KEVLAR® para-aramid synthetic fibers. The sleeve assembly 80 has an axially extending zipper closure 84 fixed to the sleeve 82. By actuating the zipper closure, the sleeve is rolled up into a tube which surrounds and receives the line 34 to thus cover the line as it extends to an inlet port 36. The zipper closure 84 has a protruding pull tab 92, which serves to advance the zipper to engage the two strips of zipper teeth 93 and close the sleeve. The pull tab 92 and portions of the sleeve are received within a box or housing 98. The protruding pull tab 92 is larger than the opening 100 in the housing, thus preventing the sleeve assembly from being extracted from the housing 98 once it is locked closed in a manner similar to the device 20 described above. Once locked inside the housing 98 the sleeve assembly 80 may not be removed without destroying the housing. Because the opening 100 must be large enough to admit the sleeve without obstruction, it does not serve as a line clamp. Hence an internal clamp may be provided in an internal wall 105. In addition, the line may have its own clamp 42. As shown in FIG. 7, the base 32 may be mounted to the limb of the patient by a bandage or dressing 112.

It should be noted that additional clamps similar to the ones 42 shown in FIG. 2, can be provided within the housing. Two clamps can be positioned within each compartment 116, 118, defined by the dividing walls 120. In each pair of clamps, one clamp 42 can have the clamp opening facing in one direction, and the other clamp 114 can have the clamp opening facing in the other direction.

It is understood that the invention is not limited to the particular construction and arrangement of parts herein illustrated and described, but embraces all such modified forms thereof as come within the scope of the following claims.

We claim:

1. A device for restricting access to a line for intravenous administration of liquids to a patient through a catheter line having an inlet port, the device comprising:

a first housing half;

a second housing half which engages with the first housing half to define a housing having an interior enclosure which receives the catheter line inlet port to prevent access thereto, the housing having clearance for the catheter line to extend outwardly from the interior enclosure, the first housing half being movable with respect to the second housing half between a first arrangement, in which the interior enclosure is accessible from the exterior of the housing to permit access to the catheter line inlet port, and a second arrangement, in which the first housing half is secured to the second housing half to prevent access to the interior enclosure from the exterior of the housing to prevent access to the catheter line inlet port; and a fastener which engages portions of the first housing half with portions of the second housing half in the second arrangement, such that the housing halves may not be returned to the first arrangement to permit access to the interior enclosure without distorting the device and giving evidence of tampering with the device.

2. The device of claim 1 further comprising:

a first tab extending from the housing second half; and a second tab extending from the housing second half opposite the first tab, the first tab and the second tab protruding from the housing second have half to provide a location for attaching the device to a user's limb by tape.

3. The device of claim 1 wherein the second housing half has an intermediate wall located within the housing compartment which defines a channel between an end wall and the intermediate wall which receives a conventional clamp that locks the PICC line.

4. The device of claim 1 further comprising:

a sleeve; and an axially extending zipper closure connected to the sleeve and actuatable to form the sleeve into a tube surrounding the line, wherein the zipper has a protruding pull tab, the pull tab being receivable within the housing when the sleeve is formed into a tube, such that the locking of the housing restricts access to the zipper and removal of the sleeve.

5. The device of claim 4 wherein the sleeve is formed of a puncture resistant material.

6. The device of claim 1 wherein a first flange extends from the first housing half, and second flange extends from the second housing half beneath the first flange, and wherein openings are formed in the two flanges to receive the fastener.

7. The device of claim 6 wherein the fastener comprises a zip tie.

8. The device of claim 6 wherein the first housing half and the second housing half are formed of plastic material, and wherein the fastener comprises a metal element with a narrower-diameter segment located between two larger-diameter segments, the fastener being driven into engagement with the housing half flanges by a press.

9. A device for restricting access to a line for intravenous administration of liquids to a patient through a catheter line having an inlet port, the device comprising:

a first housing half having a bottom wall and side walls with portions defining an inlet groove;

a second housing half, having portions which are releasably engageable with the first housing half, wherein the first housing half is engaged with the second housing half in a locked configuration to define an interior enclosure which receives the catheter line inlet port to prevent access thereto, the catheter line extending through the first housing half inlet groove;

a first flange extending from the first housing half;

a second flange extending from the second housing half to overlie the first flange in the locked configuration; and a locking fastener which extends through the first flange and the second flange to secure the first housing half to the second housing half, such that the locking fastener retains the second housing half secured to the first housing half to exclude access to the catheter line inlet port within the interior enclosure, and wherein access to the interior enclosure is prevented without distorting the device and giving evidence of tampering with the device.

10. The device of claim 9 wherein the fastener comprises a zip tie.

11. The device of claim 9 wherein the first housing half and the second housing half are formed of plastic material, and wherein the fastener comprises a metal element with a narrower-diameter segment located between two larger-diameter segments, the fastener being driven into engagement with the housing half flanges by a press.

12. The device of claim 9 further comprising:

a first tab extending from the housing second half; and a second tab extending from the housing second half opposite the first tab, the first tab and the second tab protruding from the housing second half to provide a location for attaching the device to a user's limb by tape.

13. The device of claim 9 wherein the second housing half has an intermediate wall located within the housing compartment which defines a channel between an end wall and the intermediate wall which receives a conventional clamp that locks the PICC line.

14. The device of claim 9 further comprising:

a sleeve; and an axially extending zipper closure connected to the sleeve and actuatable to form the sleeve into a tube surrounding the line, wherein the zipper has a protruding pull tab, the pull tab being receivable within the housing when the sleeve is formed into a tube, such that the locking of the housing restricts access to the zipper and removal of the sleeve.

15. The device of claim 14 wherein the sleeve is formed of a puncture resistant material.

\* \* \* \* \*